United States Patent
Taylor et al.

(10) Patent No.: US 12,393,602 B2
(45) Date of Patent: Aug. 19, 2025

(54) EXTRACTION OF RELEVANT SIGNALS FROM SPARSE DATA SETS

(71) Applicant: QUEST DIAGNOSTICS INVESTMENTS LLC, Secaucus, NJ (US)

(72) Inventors: Rebecca E. Taylor, Secaucus, NJ (US); Jennifer L. Lapierre, Secaucus, NJ (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 192 days.

(21) Appl. No.: 17/799,142

(22) PCT Filed: Feb. 12, 2021

(86) PCT No.: PCT/US2021/017867
§ 371 (c)(1),
(2) Date: Aug. 11, 2022

(87) PCT Pub. No.: WO2021/163491
PCT Pub. Date: Aug. 19, 2021

(65) Prior Publication Data
US 2023/0073952 A1    Mar. 9, 2023

Related U.S. Application Data

(60) Provisional application No. 62/976,175, filed on Feb. 13, 2020.

(51) Int. Cl.
*G06F 16/25*    (2019.01)

(52) U.S. Cl.
CPC .................. *G06F 16/254* (2019.01)

(58) Field of Classification Search
CPC ........ G06F 16/254; G16B 20/00; G16B 20/20; G16B 25/10; G16B 40/00; G16B 50/10
See application file for complete search history.

(56) References Cited

U.S. PATENT DOCUMENTS

| | | | |
|---|---|---|---|
| 10,445,312 B1* | 10/2019 | Lewis | G06F 16/22 |
| 10,460,830 B2* | 10/2019 | Glynias | G01N 33/5308 |
| 2003/0009295 A1 | 1/2003 | Markowitz et al. | |
| 2006/0052945 A1* | 3/2006 | Rabinowitz | G16H 50/70 |
| | | | 702/20 |
| 2017/0169160 A1 | 6/2017 | Hu et al. | |
| 2017/0270212 A1 | 9/2017 | Lavrenko et al. | |

(Continued)

OTHER PUBLICATIONS

Landrum et al. Sep. 26, 2017, ClinVar: Improving Access to Variant Interpretations and Supporting Evidence, https://watermark.silverchair.com (Year: 2017).*

(Continued)

*Primary Examiner* — Matthew J Ellis
(74) *Attorney, Agent, or Firm* — Foley & Lardner LLP (57) ABSTRACT

The methods discussed herein can extract relevant signals from sparse data sets, for instance in cryptographic analysis, noise reduction, pattern recognition, or computational genetics. The present solution can improve technological performance of an analytical device such as through reducing server load, computation time, and data storage sizes. The present solution can identify relevant signals, such as genetic variants with a high probability of pathogenicity, in large, sparse data sets.

15 Claims, 2 Drawing Sheets

(56) References Cited

U.S. PATENT DOCUMENTS

| | | | |
|---|---|---|---|
| 2017/0329901 A1* | 11/2017 | Chowdry | G16B 40/00 |
| 2019/0114544 A1 | 4/2019 | Sundaram et al. | |
| 2019/0228836 A1* | 7/2019 | Zhang | G16B 40/20 |
| 2020/0272915 A1* | 8/2020 | Tata | G06F 16/35 |

OTHER PUBLICATIONS

Konopka T, Nijman SM. Comparison of genetic variants in matched samples using thesaurus annotation. Bioinformatics. Mar. 1, 2016;32(5):657-63. doi: 10.1093/bioinformatics/btv654. Epub Nov. 5, 2015. PMID: 26545822; PMCID: PMC4795618. (Year: 2015).*

International Search Report and Written Opinion for PCT Appl. No. PCT/US2021/017867, mailed May 3, 2021.

Extended European Search Report dated Feb. 7, 2024 in EP 21753916.2.

* cited by examiner

EXTRACTION OF RELEVANT SIGNALS FROM SPARSE DATA SETS

CROSS-REFERENCE TO RELATED PATENT APPLICATIONS

The present application is the U.S. National Stage of PCT/US2021/017867, filed Feb. 12, 2021, which claims the benefit of and priority to U.S. Provisional Patent Application No. 62/976,175 filed Feb. 13, 2020, the entire disclosure of which is incorporated by reference herein.

FIELD OF THE INVENTION

The present invention relates generally to the field of data processing, and in particular the extraction of relevant signals from sparse data sets.

BACKGROUND

The processing of large sets of data to obtain relevant signals (e.g., data of interest for a particular diagnostic inquiry, data containing hidden or obfuscated signals within a noise floor or steganographic encoding, astrophysical data sets based on large sky surveys, etc.) is resource-intensive and inefficient, requiring a large amount of processing power, memory, and network bandwidth accessing data servers, as well as significant downstream resources to cull or vet the resulting data. In the absence of a method to extract relevant signals, downstream validation procedures for data relevance also require inefficient, intense resource usage. Upstream methods for extraction of signals might involve sophisticated machine learning algorithms, or manual curation and of databases, but these either require significant computational power and storage space, or require significant human intervention that cannot practically consider the entirety of the underlying data sets.

For instance, genetic testing and computational genetics generally suffer from the problem of huge but sparse data sets that occupy immense amounts of storage space and require immense computing power, yet contain relatively few relevant items of data for a given scientific inquiry. This is especially true because genetic information, for instance genetic variant information, is frequently split between many such databases that may or may not overlap in content, so as to be either redundant or complementary.

Similarly, signals may be hidden within noise of other data such as images, audio, radio signals, etc., by adding a few bits of the hidden signal at various intervals in time and/or frequency. By providing the signal as sparse data within noise or other signals, the signal may be hidden from most interception. However, it may still be possible to detect such signals through a brute force scanning approach, though this may require extensive computing power and bandwidth.

SUMMARY OF THE INVENTION

The systems and methods disclosed herein provide for extraction of relevant signals from sparse data sets, and in some implementations may filter or exclude noise from such data sets. This may reduce processing requirements compared to analyzing entire data sets including low quality, irrelevant, or erroneous data and can increase computational speeds by reducing the amount of computational time spent on data that may provide inaccurate or irrelevant results. In many implementations, these systems and methods may also reduce memory and bandwidth consumption relative to processing or transferring entire data sets.

According to at least one aspect of the disclosure, a method to extract relevant data from sparse data sets can include collecting, by an analysis device, data from a first sparse data set, each item of data in the first sparse data set comprising a first identifier; comparing, by the analysis device, a number of items of data of the first sparse data set having a first value for the first identifier to a predefined threshold; and collecting, by the analysis device, additional data from at least one additional data set when the number of items of data of the first sparse data set having the first value for the first identifier is below the predefined threshold, the at least one additional data set comprising data corresponding to at least one item of data in the first sparse data set, and wherein each item of data in the at least one additional data set lacks the first identifier. The additional data set can also be sparse.

In some implementations, the first sparse data set comprises a genetic variant database. In some implementations, the at least one additional data set comprises at least one additional genetic variant database. In some implementations, the genetic variant database comprises human genetic variant data. In some implementations, the at least one additional genetic variant database comprises human genetic variant data. In some implementations, each item of data comprises information identifying a genetic variant. In some implementations, the first value comprises an indication of loss-of-function status corresponding to the genetic variant identified in the item of data.

In some implementations, the method is performed with a first set of parameters to generate a first set of relevant signals; and performed at least one additional time with at least one additional set of parameters to generate at least one additional set of relevant signals.

According to at least one aspect of the disclosure, a method to extract relevant data from sparse data sets can include collecting, by an analysis device, a plurality of data records from a first sparse data set, each data record comprising a first identifier, and at least one first value; and for each data record, comparing, by the analysis device, the at least one first value with a first predefined signal criterion and a first predefined noise criterion; and, either (i) when the at least one first value corresponds to the first predefined noise criterion, discarding the data record; or (ii) when the at least one first value does not correspond to either the first predefined signal criterion or the first predefined noise criterion, (1) collecting, by the analysis device, additional data from at least one additional data set, wherein the at least one additional data set comprises an additional identifier corresponding to the first identifier of the data record, and wherein the additional data comprises at least one second value; (2) comparing, by the analysis device, the at least one second value with a second predefined signal criterion; and (3) discarding, by the analysis device, the data record unless the at least one second value corresponds to the second predefined signal criterion. The additional data set can also be sparse.

In some implementations, the method is performed with a first set of parameters to generate a first set of relevant signals; and performed at least one additional time with at least one additional set of parameters to generate at least one additional set of relevant signals.

In some implementations, the at least one second value is generated after the step of collection of additional data from at least one additional data set. In some implementations, the at least one additional data set comprises a plurality of additional data sets.

In some implementations, the at least one second value comprises a count of data sets within the at least one additional data set comprising an additional identifier corresponding to the first identifier of the data record.

In some implementations, the first sparse data set comprises a genetic variant database. In some implementations, the genetic variant database comprises human genetic variant data. In some implementations, the at least one additional data set comprises at least one additional genetic variant database. In some implementations, the at least one additional genetic variant database comprises human genetic variant data. In some implementations, the first identifier identifies a genetic variant. In some implementations, the additional identifier defines a genetic variant. In some implementations, the at least one first value corresponds to an indication of a phenotype of the genetic variant. In some implementations, the first predefined signal criterion comprises an indication of a loss-of-function phenotype corresponding to the genetic variant. In some implementations, the first predefined signal criterion comprises an indication of a pathogenic phenotype corresponding to the genetic variant. In some implementations, the first predefined noise criterion comprises a predefined genetic variant carrier frequency range. In some implementations, the second predefined signal criterion comprises a predefined range for a count of data sets.

According to at least one aspect of the disclosure, a system for extracting relevant data includes an analysis device comprising a memory unit and a processing unit and a storage unit in communication with the analysis device, wherein the storage unit is configured to receive relevant signals extracted by the analysis device. The analysis device is configured to extract relevant signals by performing the steps comprising (1) collecting a plurality of data records from a first sparse data set, wherein the first sparse data set comprises a plurality of data records, each data record comprising a first identifier and at least one first value; (2) for each data record: comparing the at least one value with a first predefined signal criterion and a first predefined noise criterion; and either (i) when the at least one first value corresponds to the first predefined noise criterion, discarding the data record; or (ii) when the at least one first value does not correspond to either the first predefined signal criterion or the first predefined noise criterion: (a) collecting additional data from at least one additional data set, wherein the collected data comprises an additional identifier corresponding to the first identifier of the data record; (b) comparing the at least one second value with a second predefined signal criterion; and (c) discarding the data record the at least one second value corresponds to the second predefined signal criterion; and (3) storing each non-discarded data record on the storage unit. Any additional data set can also be sparse.

In some implementations, the at least one second value is generated after the step of collection of additional data from at least one additional data set. In some implementations, the second predefined signal criterion comprises a predefined range for a count of data sets. In some implementations, the at least one additional data set comprises a plurality of additional data sets. In some implementations, the at least one second value comprises a count of data sets within the at least one additional data set comprising an additional identifier corresponding to the first identifier of the data record.

In some implementations, the first sparse data set comprises a genetic variant database. In some implementations, the at least one additional data set comprises at least one additional genetic variant database. In some implementations, the genetic variant database comprises human genetic variant data. In some implementations, the at least one additional genetic variant database comprises human genetic variant data. In some implementations, the first identifier identifies a genetic variant. In some implementations, the at least one first value corresponds to an indication of a phenotype of the genetic variant. In some implementations, the first predefined signal criterion comprises an indication of a loss-of-function phenotype corresponding to the genetic variant. In some implementations, the first predefined signal criterion comprises an indication of a pathogenic phenotype corresponding to the genetic variant. In some implementations, the first predefined noise criterion comprises a predefined genetic variant carrier frequency range.

According to at least one aspect of the disclosure, a system for extracting relevant signals from sparse data sets includes an analysis device comprising a memory unit and a processing unit; and a storage unit in communication with the analysis device, wherein the storage unit is configured to receive relevant signals extracted by the analysis device. The analysis device is configured to extract relevant signals by performing the steps comprising: (1) collecting data from a first sparse data set, each item of data in the first sparse data set comprising a first identifier; (2) comparing a number of items of data of the first sparse data set having a first value for the first identifier to a predefined threshold; and (3) collecting, by the analysis device, additional data from at least one additional data set when the number of items of data of the first sparse data set having the first value for the first identifier is below the predefined threshold, the at least one additional data set comprising data corresponding to at least one item of data in the first sparse data set, and wherein each item of data in the at least one additional data set lacks the first identifier; and (4) storing non-discarded data on the storage unit. Any additional data set can also be sparse.

In some implementations, the first sparse data set comprises a genetic variant database. In some implementations, the at least one additional data set comprises at least one additional genetic variant database. In some implementations, the genetic variant database comprises human genetic variant data. In some implementations, the at least one additional genetic variant database comprises human genetic variant data. In some implementations, each item of data comprises information identifying a genetic variant. In some implementations, the first value comprises an indication of loss-of-function status corresponding to the genetic variant identified in the item of data.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The foregoing and other objects, aspects, features, and advantages of the present solution will become more apparent and better understood by referring to the following description taken in conjunction with the accompanying drawings, in which.

The features and advantages of the present solution will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Unless otherwise defined, all technical and scientific terms used herein have the same meaning as commonly understood by one of ordinary skill in the art to which the present technology belongs. Additionally, in some instances, definitions may be provided herein as alternate definitions in addition to the meaning as commonly understood by one of ordinary skill in the art; accordingly, any definitions provided herein should be considered in addition to the ordinary meaning rather than exclusive of the ordinary meaning, unless explicitly specified.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

The term "analysis device" describes a computing device, such as a laptop computer, desktop computer, portable computer, tablet computer, wearable computer, embedded computer, computing appliance, workstation, server, or a plurality of such computing devices, including virtual machines executed by one or more physical devices (e.g. a cloud, cluster, or farm).

Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

In some instances, the term "value" means a piece of data within a data record or a piece of data describing some aspect of one or more data records. For example, a description of the phenotype associated with a variant in a database entry for that variant would be a value. As another example, a count of the number of databases that an identifier appeared in would be a value.

In some instances, the term "identifier" means a value used to identify (or index) a particular item of data, such as a unique or semi-unique string or value or a label, or any other such data or value that may be used to identify an item of data or other entity, including a name, a counter value, an index value, a sequence value, or any other such data. Examples of identifiers include accession numbers, names assigned to specific genetic variants, or database primary-key entries.

In some instances, the term "information identifying a genetic variant" includes identifiers or any other information that indicates the identity of a genetic variant.

In some instances, the term "sparse data" means data in which null or zero values are significantly more prevalent than non-zero values, frequently at least an order of magnitude more prevalent, and in many implementations, two, three, or more orders of magnitude more prevalent. In this sense, "null or zero values" and "non-zero" values can be determined by comparison of data values to a relevance criterion. In many implementations, "null or zero values" may be absent or removed, and thus may not explicitly refer to items, data, entries, or other entities having zero values, but rather gaps between other non-zero data.

In some instances, the term "database" as used herein includes the examples recited herein, such as common genetic variant databases, as well as analogous databases. In various implementations and uses, the term includes, for example, gnomAD, including gnomAD v2 and v3 databases; the astrophysics data system (ADS) provided by the National Aeronautics and Space Administration (NASA); the Food and Drug Administration's adverse event reporting system (FAERS); or any other such data set.

Where technical features in the drawings, detailed description, or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

In some embodiments, the systems and methods described herein may be applied in the context of genetics. For example, genetic screening often relies on the detection of variants that are present at very low rates in the general population. Such screening is limited by the fact that the scientific significance of many variants often requires downstream validation after data collection, and the fact that genetic information is big. The human genome, for instance, constitutes over 3 billion base pairs; in addition to gene-sequence information, genetic variant databases often include other information such as gene function annotations, bibliographical information, and other data that swell their size and complexity. On the other hand, such data sets, while requiring extensive computational power and storage capacities, often contain relatively little data that is relevant. The systems and methods here can improve computational technology and conserve resources by reducing the amount of computation time and storage resources needed in this process.

The literature describes several genetic databases containing information on human genetic variants. For instance, particularly relevant databases include gnomAD, OMIM, ClinVar, HGMD, and other, disease-specific databases. Genomic databases each have strengths and weaknesses when used individually, and analyses thus often require information sourced from multiple databases.

In some embodiments, the technology disclosed provides a method for extracting relevant signals (that is, genetic variants having a high probability of pathogenicity) from sparse data sets (that is, human genetic variant databases).

One embodiment entails a method for extracting relevant genetic variants from human genetic variant databases. The method includes first the step of collecting, by an analysis device, data from a first sparse data set. The sparse data set is a genetic variant database, which may be a commercially available or publicly available database (such as gnomAD), an internal database, and may be a database in its entirety or one that has been pre-filtered to include only particular genes or variants matching predefined criteria. The sparse data set may also include entries from multiple genetic variant databases (such as gnomAD in conjunction with OMIM, Clinvar, and others). This collected data contains a first identifier, such as an accession number or other unique identifier that ties the data to a particular genetic variant and can be used to find correlated data in other data sets, and a first value for the first identifier, such as an indication (direct or indirect) that the variant corresponding to the identifier results in a loss-of-function phenotype. The method next includes the step of comparing, by the analysis device, to a predefined threshold the number of items of data (i.e., genetic variants) of the first sparse data set that have the first value for the first identifier. For instance, the number of variants selected might be compared against a desired number to include in a screen, or a desired number that is needed to ensure an adequate detection rate for the disease of interest. If that threshold is not met, an additional collecting step, by the analysis device, is performed in which additional data from at least one additional data set (e.g., additional gene variant databases, which may include formal databases or a collection of data about gene variants assembled from scientific literature) is collected. This additional data may also be pre-filtered, and the additional data each lack the identifiers of the first set of collected data (i.e., they are not redundant).

Another embodiment entails a method for extracting relevant genetic variants from human genetic variant databases. The method includes first the step of collecting, by an analysis device, a plurality of data records from a first sparse data set. The sparse data set is a genetic variant database, which may be a commercially available or publicly available database (such as gnomAD), an internal database, and may be a database in its entirety or one that has been pre-filtered to include only particular genes or variants matching predefined criteria. The sparse data set may also include entries from multiple genetic variant databases (such as gnomAD in conjunction with OMIM, Clinvar, and others). Each collected data record contains a first identifier, such as an accession number or other unique identifier that ties the data to a particular genetic variant and can be used to find correlated data in other data sets, and a first value for the first identifier, such as an indication (direct or indirect) that the variant corresponding to the data record results in a loss-of-function phenotype, or an indication of the genotypic or phenotypic character of the variant, or a flag indicating the presence of the variant in the database. The method next includes the step of comparing, for each data record, the value with a first predefined signal criterion (e.g., that the genetic variant will result in a loss-of-function phenotype) and a first predefined noise criterion (e.g., that the genetic variant has no phenotypic effect, or that the genetic variant does not correspond to a gene of interest). Either criterion may contain a plurality of subcriteria. If the value corresponds to the noise criterion, it is discarded. If it corresponds to the signal criterion, it is kept. If it corresponds to neither, the method includes an additional collecting step, by the analysis device, in which additional data from at least one additional data set (e.g., additional gene variant databases, which may include formal databases or a collection of data about gene variants assembled from scientific literature) is collected. This additional data may also be pre-filtered, and the additional data contain at least one second value. The second value may be one calculated after data collection, such as a count of the number of databases that data corresponding to the variant was found in. The method then includes the step of comparing, by the analysis device, the second value, if applicable, to a second predefined signal criterion (e.g., that the genetic variant is present in multiple databases), and discarding, by the analysis device, the data record unless the at least one second value corresponds to the second predefined signal criterion.

In another embodiment, a system for selecting variants is described. This system comprises an analysis device comprising a memory unit and a processing unit, as well as a storage unit in communication with the analysis device, wherein the storage unit is configured to receive relevant signals extracted by the analysis device. This may entail a bioinformatics server with processors, RAM, and storage memory, or a virtual machine, or a cloud service, or similar. The system also interacts with a first sparse data set and at least one additional data set. The analysis device is configured to perform the methods discussed herein.

The following example illustrates the use of the method disclosed here to extract relevant genetic variants for the purposes of a multi-gene diagnostic screen. In particular, the screen is directed to detection of variants that indicate that a patient is a potential carrier of a heritable disease. Although discussed below primarily in terms of identifying genetic variants, as discussed above, the systems and methods discussed herein may be utilized in many other applications and industries.

Genes that are selected for review and selection of variants must meet one or more of several criteria: (1) carrier frequency that is elevated in one or more populations; (2) clinical significance (e.g., early onset; life threatening; potentially treatable); (3) pan-ethnic status (seen in multiple populations); and (4) high detection rate reported in the literature for one or more populations.

Genes of interest include genes that correspond to known heritable disease. For instance, the gene FKTN, corresponding to fukutin, is selected for Walker-Warburg Syndrome. Other genes of interest are shown in Table 1.

TABLE 1

Genes of Interest for Variant Selection

| Disease State | Gene |
|---|---|
| Abetalipoproteinemia | MTTP |
| Adrenoleukodystrophy, X-Linked | ABCD1 |
| Alpha-Thalassemia | HBA1/ HBA2 |
| Argininosuccinic aciduria (ASL) | ASL |
| Ataxia-telangiectasia (ATM) | ATM |
| Bardet-Biedl syndrome, BBS1-related | BBS1 |
| Bardet-Biedl syndrome, BBS2-related | BBS2 |
| Beta-Hemoglobinopathies (inc. Sickle Cell) | HBB |
| Biotinidase Deficiency (BTD) | BTD |
| Bloom syndrome | BLM |
| Canavan Disease | ASPA |
| Carnitine palmitoyltransferase II deficiency | CPT2 |
| Cerebrotendinous Xanthomatosis | CYP27A1 |
| Citrullinemia, type 1 | ASS1 |
| Congenital amegakaryocytic thrombocytopenia | MPL |
| Congenital disorder of glycosylation type 1a | PMM2 |
| Cystic Fibrosis | CFTR |
| Cystinosis | CTNS |
| D-bifunctional protein deficiency | HSD17B4 |
| Dihydrolipoamide Dehydrogenase Deficiency | DLD |
| Factor XI Deficiency | F11 |
| Familial Dysautonomia | IKBKAP |
| Familial Hyperinsulinism | ABCC8 |
| Familial Mediterranean fever | MEFV |
| Fanconi Anemia group C | FANCC |
| Fragile X with reflex CGG repeats | FMR1 |
| Galactosemia, GALT-related | GALT |
| Gaucher disease | GBA |
| Glutaric acidemia type 1 | GCDH |
| Glycogen Storage Disease, Type Ia | G6PC |
| Glycogen storage disease, type IV | GBE1 |
| Glycogen storage disease, type III (AGL) | AGL |
| Glycogen Storage Disease: Type II (Pompe Disease) | GAA |
| GRACILE syndrome (BCS1L) | BCS1L |
| Hereditary fructose intolerance (ALDOB) | ALDOB |
| Hermansky-Pudlak Syndrome, HPS1-Related | HPS1 |
| Hermansky-Pudlak Syndrome, HPS3-Related | HPS3 |

TABLE 1-continued

Genes of Interest for Variant Selection

| Disease State | Gene |
|---|---|
| Hypophosphatasia, autosomal recessive | ALPL |
| Joubert Syndrome 2 | TMEM216 |
| Krabbe disease | GALC |
| Limb-Girdle Muscular Dystrophy, Type 2A (CAPN3) | CAPN3 |
| Limb-Girdle Muscular Dystrophy, Type 2D (SGCA) | SGCA |
| Long-chain 3-hydroxyacyl-CoA dehydrogenase deficiency (LCHAD) | HADHA |
| Maple Syrup Urine Disease, 1A and 1B | BCKDHA/ BCKDHB |
| Medium Chain Acyl-CoA Dehydrogenase Deficiency (MCAD) | ACADM |
| Metachromatic leukodystrophy | ARSA |
| Methylmalonic Aciduria & Homocystinuria, type cbIC (MMACHC) | MMACHC |
| Mucolipidosis type II and III, GNPTAB-related | GNPTAB |
| Mucolipidosis type IV | MCOLN1 |
| Mucopolysaccharidosis, type I (Hurler syndrome) | IDUA |
| Mucopolysaccharidosis, Type IIIA (Sanfilippo Syndrome A) (SGSH) | SGSH |
| Nemaline Myopathy | NEB |
| Nephrotic syndrome, NPHS1-related (Congenital Finnish Nephrosis) | NPHS1 |
| Neuronal ceroid-lipofuscinosis, CLN3-related | CLN3 |
| Neuronal ceroid-lipofuscinosis, CLN5-related | CLN5 |
| Neuronal ceroid-lipofuscinosis, CLN8-related | CLN8 |
| Neuronal ceroid-lipofuscinosis, PPT1-related | PPT1 |
| Neuronal ceroid-lipofuscinosis, TPP1-related | TPP1 |
| Niemann-Pick Disease, types A & B | SMPD1 |
| Nijmegen breakage syndrome | NBN |
| Nonsyndromic Hearing Loss and Deafness: GJB6 Related DFNB1 | GJB6 |
| Non-Syndromic Hearing Loss, GJB2-Related | GJB2 |
| Ornithine transcarbamylase deficiency (OTC) | OTC |
| Pendred Syndrome and DFNB4 hearing loss (SLC26A4) | SLC26A4 |
| Phenylketonuria (PKU) | PAH |
| Polycystic kidney disease, autosomal recessive | PKHD1 |
| Primary hyperoxaluria type 1 (AGXT) | AGXT |
| PROP1-Related Combined Pituitary Hormone Deficiency (PROP1) | PROP1 |
| Propionic acidemia, PCCA-related | PCCA |
| Propionic acidemia, PCCB-related | PCCB |
| Short Chain Acyl-CoA Dehydrogenase Deficiency | ACADS |
| Sjogren-Larsson syndrome (ALDH3A2) | ALDH3A2 |
| SLC26A2-RELATED CONDITIONS - Sulfate transporter-related osteochondrodysplasias, includes achondrogenesis type 1B, atelosteogenesis type 2, diastrophic dysplasia, and recessive multiple epiphyseal dysplasia AND Atelosteogenesis Type 2 | SLC26A2 |
| Smith-Lemli-Opitz syndrome | DHCR7 |
| Spinal Muscular Atrophy with reflex includes g.27134T > G variant | SMN |
| Systemic primary carnitine deficiency | SLC22A5 |
| Tay-Sachs | HEXA |
| Tyrosinemia type 1 | FAH |
| Usher Syndrome, Type IF | PCDH15 |
| Usher Syndrome, Type IIIA | CLRN1 |
| Usher Syndrome: Type 2A (USH2A) | USH2A |
| Very long-chain acyl-CoA dehydrogenase deficiency (VLCAD) | ACADVL |
| Walker-Warburg Syndrome | FKTN |
| Wilson disease | ATP7B |
| Zellweger spectrum disorder, PEX2-related | PEX2 |
| 2-Methyl-3-hydroxybutyric aciduria; aka 3-ketothiolase deficiency | ACAT1 |
| 3-Hydroxy-3-methylglutaric aciduria aka HMG-CoA Lyase deficiency, HL deficiency | HMGCL |
| 3-Methylcrotonyl-CoA carboxylase deficiency -type 1 | MCCC1 |
| 3-Methylcrotonyl-CoA carboxylase deficiency type 2 | MCCC2 |
| 6-pyruvoyl-tetrahydropterin Synthase Deficiency | PTS |
| Adenosine deaminase deficiency | ADA |
| Alpha-mannosidosis | MAN2B1 |
| Alport syndrome, COL4A3-related | COL4A3 |
| Alport Syndrome, COL4A4-related | COL4A4 |
| Andermann syndrome (SLC12A6) | SLC12A6 |
| Arthrogryposis, mental retardation, and seizures (AMRS) | SLC35A3 |
| Aspartylglycosaminuria | AGA |

TABLE 1-continued

Genes of Interest for Variant Selection

| Disease State | Gene |
|---|---|
| ATP7A-related Disorders | ATP7A |
| Autoimmune Polyglandular Syndrome, Type 1 | AIRE |
| Autosomal Recessive Congenital Ichthyosis, TGM1 Related (TGM1)/Lamellar Ichthyosis, Type 1 | TGM1 |
| Autosomal recessive spastic ataxia of Charlevoix-Saguenay (ARSACS) | SACS |
| Bardet-Biedl syndrome, BBS10-related | BBS10 |
| Cartilage-hair hypoplasia | RMRP |
| Alport Syndrome, X-linked - COL4A5 | COL4A5 |
| Familial/congential Hyperinsulinism | KCNJ11 |
| Deafness, Autosomal Recessive 77 | LOXHD1 |
| Dyskeratosis Congenita, RTEL1-Related | RTEL1 |
| Fanconi Anemia group A | FANCA |
| Glycine encephalopathy, AMT-related | AMT |
| Glycine encephalopathy, GLDC-related | GLDC |
| Glycogen storage disease, type Ib (SLC37A4) | SLC37A4 |
| GM1 gangliosidosis and mucopolysaccharidosis type IVB, Morquio Syndrome (GLB1) | GLB1 |
| Holocarboxylase synthetase deficiency | HLCS |
| Homocystinuria, CBS-related | CBS |
| Hydrolethalus Syndrome | HYLS1 |
| Inclusion Body Myopathy 2 | GNE |
| Infantile Cerebral and Cerebellar Atrophy (MED17) | MED17 |
| Isovaleric Acidemia | IVD |
| Junctional epidermolysis bullosa, LAMA3-related | LAMA3 |
| Junctional epidermolysis bullosa, LAMB3-related | LAMB3 |
| Junctional Epidermolysis Bullosa: LAMC2 Related (LAMC2) | LAMC2 |
| LAMA2-related Muscular Dystrophy (Congenital muscular dystrophy type 1A) | LAMA2 |
| Leber Congenital Amaurosis, Type CEP290 | CEP290 |
| Leigh syndrome, French Canadian type (LRPPRC) | LRPPRC |
| Lethal Congenital Contracture Syndrome 1 (GLE1) | GLE1 |
| Limb-Girdle Muscular Dystrophy, Type 2E (SGCB) | SGCB |
| Lysinuric Protein Intolerance (SLC7A7) | SLC7A7 |
| Maple Syrup Urine Disease Type II (DBT) | DBT |
| Methylmalonic acidemia, MMAA-related | MMAA |
| Methylmalonic acidemia, MMAB-related | MMAB |
| Methylmalonic acidemia, MUT-related | MUT |
| Mucopolysaccharidosis Type II, Hunter (IDS) | IDS |
| Mucopolysaccharidosis Type IIIB | NAGLU |
| Mucopolysaccharidosis, Type IIIC, Sanfilippo C (HGSNAT) | HGSNAT |
| Mucopolysaccharidosis, Type IIID Sanfilippo D (GNS) | GNS |
| Mucopolysaccharidosis, Type VI, Maroteaux-Lamy Syndrome (ARSB) | ARSB |
| Nephrotic syndrome, NPHS2-related | NPHS2 |
| Neuronal Ceroid Lipofuscinosis, CLN6 Related (CLN6) | CLN6 |
| Niemann-Pick dz type C1/D (nova scoria type) | NPC1 |
| Pyruvate Carboxylase Deficiency | PC |
| Retinitis pigmentosa 59 - autosomal recessive (DHDDS) | DHDDS |
| Rhizomelic Chondrodysplasia Punctata, type 1 (PEX7) | PEX7 |
| Sandhoff disease | HEXB |
| Spondylothoracic Dysostosis MESP2 [TYPE 2] | MESP2 |
| Tyrosine Hydroxylase Deficiency (aka Segawa syndrome) | TH |
| Tyrosinemia Type II | TAT |
| Usher Syndrome: Type 1B (MYO7A) | MXO7A |
| Usher Syndrome: Type 1C (USH1C) | USH1C |
| Usher Syndrome: Type 1D (CDH23) | CDH23 |
| Zellweger spectrum disorder, PEX1-related | PEX1 |
| Zellweger spectrum disorder, PEX6-related | PEX6 |
| Duchene/Becker Muscular Dystrophy (DMD) | DMD |
| Pyruvate dehydrogenase deficiency (aka Leigh syndrome) | PDHA1 |
| Agammaglobulinemia, X-linked 1 (BTK) | BTK |

Variants are gathered from multiple databases, from which data are gathered and combined. Variants are gathered first from a primary database, gnomAD, which is selected for its breadth of coverage, including at least 123, 136 exome sequences and 15,496 whole-genome sequences from unrelated individuals, including numerous ethnic sub-populations (African/African American, Latino, Ashkenazi Jewish, East Asian, Finnish, Non-Finnish European, South Asian, Other). Previous methods have relied on the frequency of variants found in published studies, but many of those studies had small cohorts that do not accurately represent the larger population. Gathering from additional databases is performed as needed for determination of the relevance of a particular variant—for instance, based on an indication from gnomAD about the likely phenotype (such as loss of function) associated with the variant.

In this sense, a number of signal criteria (signifiers that a variant is of interest) and noise criteria (signifiers that a variant is not pathogenic and need not be included) can be used. A signal criterion might be that the consequence of the genetic variant is a loss-of-function phenotype or that the variant appears in multiple databases. A noise criterion might be, for instance, that a variant does not correspond to the gene of interest, does not result in a phenotype (e.g., a sense mutation), or does not appear in multiple databases.

Variants are ranked or classified into tiers by likelihood of pathogenicity based on type of variant (e.g., predicted phenotype; effect of mutation) and inclusion in multiple databases without fully reviewing each variant. Classification may be according to a heuristic or other rule. For example, a variant might be classified as potentially pathogenic if it is predicted to result in a loss of function mutation. Or a variant might be classified as potentially pathogenic if it results in a frameshift mutation, a deletion, an insertion, a nonsense mutation, or a missense mutation in a known gene active site. Classification might be based on whether the mutation is at a known or bioinformatically predicted active site of a protein encoded by the gene in which the mutation is found. Still further, a variant might be classified as potentially pathogenic if it is found in three of four databases, or some other frequency-based metric. This step may be described in some implementations as a frequency-based data filter across data sets. Classification might also use multiple heuristics in combination, such as satisfying either (1) the presence of a variant in multiple databases or (2) a predicted loss of function phenotype for the variant. Alternatively, a machine-learning-based classifier using a supervised data set of known or highly likely pathogenic variants can be used. As another option, an unsupervised machine learning classifier may be used. Such classifications may be performed at this early step of the process without needing to analyze additional characteristics of the variant. Ranking may include multiple tiers: for instance, Tier I (variants having the highest probability of pathogenicity by virtue of either being loss-of-function variants or included in multiple databases) and Tier II (all probable pathogenic variants). In other implementations analyzing other data types and applications, the tier I data set may comprise portions of data signals likely to be of interest, relative to tier II data set of all data signals. Accordingly, in some implementations, the tier I data set may be a subset of the tier II data set, and may be referred to as a filtered set, a subset, an interest set, or any other corresponding term.

For instance, the methods used herein can generate a Tier I list using the following parameters:

TABLE 2

Example Parameters

| Parameter | Content |
|---|---|
| First value | Phenotypic consequence of genetic variant. |
| First sparse data set | gnomAD database. |
| Additional data set | ClinVar, OMIM, HGMD, and disease-specific databases |
| First predefined signal criterion | Variant corresponds to loss-of-function phenotype for gene of interest. |

TABLE 2-continued

Example Parameters

| Parameter | Content |
|---|---|
| First predefined noise criterion | Variant does not related to gene of interest. |
| Second value | Count of databases containing genetic variant. |
| Second predefined signal criterion | Genetic variant is present in multiple databases. |

As an additional check step, in many implementations, carrier frequency (i.e., population genotype frequency) or disease prevalence (i.e., population phenotype frequency) from the literature can be compared to find what the frequency of predicted pathogenic variants found in gnomAD should be.Such comparisons can be performed, for example, using standard genetic principles such as the Hardy-Weinberg equation, which can be used to relate a phenotype frequency for a recessive trait to a genotype frequency. This comparison can be done by setting a threshold against which the number or combined frequency of variants is compared, and collection additional data if the threshold is not met. This serves to check as well whether gnomAD is capturing a wide enough distribution of variants for a given disease or gene. For instance, if known population disease prevalence is inconsistent with the frequency of potentially pathogenic variants found for that population, this indicates that the variant selection has potentially been underinclusive and that detection rates in a genetic screening based on the selection would be inaccurate, and that further data should be queried from further databases and the literature to find additional variants. This comparison can be done within a particular subpopulation.

Variants (or portions of data signals of interest) are then selected based on detection rates. A highly inclusive screen (e.g., corresponding to Tier 2) will have a high detection rate but be resource-intensive. A more measured screen including fewer variants (e.g., corresponding to Tier 1) will have a lower detection rate but be less resource-intensive. Detection rate across sub-portions of the data (e.g., ethnic sub-populations) may vary, and so a detection rate may be set for each sub-portion of the data (or subpopulation). See, e.g., Table 3. This detection rate can serve as a threshold to guide whether additional data collection or discarding is required.

where a threshold for acceptable variant count within a tier is not met. Alternatively, additional databases can be included within the secondary-database criteria in the frequency-based filtration above. Variants from reputable disease-specific databases may be included when applicable. For example, the CFTR2 database may be used for cystic fibrosis (CF)-related variants that may not be present in other less CF-rich databases. As another example, copy number variations (CNVs) are not included in gnomAD but are available in ExAC. And, further, Middle Eastern populations are generally not included in gnomAD, so the published literature and databases can be used to find applicable variants and calculate detection rates.

Once a list of variants is generated, the variants are vetted to ensure that they correspond to pathogenicity. The variant-selection step prioritizes inclusion of variants with a higher probability of pathogenicity, meaning that the majority of variants at this step require only truncated annotation time. Some variants, however, will require further vetting. Variants may be vetted through in vivo, in vitro, or in silico methods. For example, a variant can be vetted through clinical trials or clinical study of patients identified to have the variant. As another example, a variant could be vetted through laboratory study of cell lines with the variant, either collected from human subjects or genetically engineered. As still another example, a variant could be vetted through computational methods, such as biophysical simulation or modeling, bioinformatics prediction of the effect of the variant, by inspection of the site and nature of any mutations within the variant in view of the known structure or function of the gene, or by gathering of additional data related to the variant from additional databases. Many variants selected by the above method will need essentially no vetting, such as variants with known pathogenicity or with clear loss-of-function mutations. Variants of unknown significance (VUS, also known as variants of uncertain significance) are excluded, such that the relevant signal set comprises actionable variants that can be reasonably vetted. A variant can be classified as a VUS, for example, if there is no apparent or feasible hypothesis connecting the variant and pathogenicity, such as with a conservative amino acid mutation. Alternatively, a VUS might be any variant for which the association with disease risk is unclear. The threshold for VUS

TABLE 3

Detection Rate by Ethnic Subpopulation

| | | Estimated Detection Rate by Ethnic Subpopulation | | | | | | |
|---|---|---|---|---|---|---|---|---|
| Method | Number of Variants | African | Ashkenazi Jewish | East Asian | European (Finnish) | European (Non-Finnish) | Latino | Other | South Asian |
| QHerit 1 | 1 | 0% | 98% | 0% | 0% | 3% | 31% | 0% | 0% |
| Tier 1 variants only | 20-35 | 10% | 98% | 9% | 15% | 37% | 32% | 0% | 38% |
| Tier 1 + Tier 2 | 75-100 | 79% | 98% | 72% | 83% | 83% | 68% | 75% | 79% |

Tier 1-determined to have a higher chance of being pathogenic based on data pull
Tier 2-comprehensive list of all probable pathogenic variants Additional variant-selection steps can be used to complement the above steps when the number of variants is not high enough for the desired detection rates in the desired populations. For example, additional databases can be queried to concatenate the results from the primary database screen classification can be tuned to affect the degree of vetting and further database or other resource usage required.

The above steps represent a novel and comprehensive approach to variant selection, especially variant selection for screening for inheritable diseases. The method entails the ability to rely on a much larger data collection than limited published cohorts. Additionally, the method results in selection of variants that maximize detection rate across subpopulations and returns actionable, relevant variants.

The following example illustrates the use of the method disclosed here to aid the rapid and efficient translation of text.

There is increased need for on-demand translation of text. For instance, medical and emergency personnel responding to disasters in resource-poor or economically underdeveloped areas may not be familiar with the language of the disaster location. Yet understanding written communications in such language might be crucial for personnel to interact with local residents and emergency services. Such environments also may have a lack of reliable and fast network connectivity, and personnel may be limited to the use of personal devices with limited computing ability and storage space.

A method according to the disclosure can be used to increase the technological performance of a device (e.g., cell phone, tablet, or personal computer), for example, used to translate text in near real time. Besides a personal device, the method might be used by a server that handles all the web or other communication for an organization. In response to a text string to be translated, the device collects data from a first sparse data set, such as a translation database. The translation database might be on the device or accessed remotely. This collection occurs as part of a machine translation step that returns a suggested translation based on the translation database, as well as a confidence score based on the predicted accuracy of the text. The collection then returns the string portioned into substrings (i.e., data records) and their associated translations. The text of each substring can serve as the identifier in the method, and the confidence score can serve as the first value.

A predefined signal criterion can be set. For example, the signal criterion might be a particular confidence score below which additional data is required for accurate translation of the substring. The threshold confidence score can be adjusted to allow a real-time tradeoff between accuracy and resource usage, allowing a user to adjust, for example, to an event in which telecommunications lines are suddenly inundated and network communication strength is poor. A predefined noise criterion can also be set. For example, a substring can be discarded if it does not appear to correspond to intelligible text, such as being an emoji, a string of numbers, ASCII art, or a pictogram not in the language to be translated. This can be reflected in the confidence score. For example, the confidence score might be configured to include the ranges 0-5 (translation not possible; not intelligible text), 6-75 (additional data required), and 75-100 (initial translation adequate).

The method then entails comparing the confidence score to the signal and noise criteria. If the noise criterion is met, the substring is discarded and not translated. If the signal criterion is met, the substring and its translation are retained. If neither condition is met, additional data is collected. The additional data includes, for example, a translation performed of the substring based on an additional language database, and optionally an additional machine translation program that can be located on a remote server. The additional language database can be much larger and more sophisticated than the first, and can employ more sophisticated and technologically demanding hardware and software. The additional data then includes a second value (i.e., a second confidence score based on the new translation) and second signal criterion (i.e., a threshold for the second confidence score) for a similar gating comparison. Based on the results of the second comparison, the method can retain the original translation (if the second is worse), retain the second (if the original is worse), or retain both and present them as alternative suggestions.

The above steps represent a novel and comprehensive approach to translation, especially translation using limited technology, including limited local storage space and processing power.

Other applications of the disclosed systems and methods include in noise reduction or cryptography, by virtue of filtering out non-relevant signals and selecting signals for further collection. Other applications include evaluation of large-scale toxicology studies or databases, or other biomedical data, in which the systems and methods can isolate pertinent data for follow-up or screening. Other applications include large-scale machine translation of massive corpora of text, in which reliable, straightforward translated words or phrases can be retained and unreliable portions of the translation can result in collection of further data, in the form of additional machine or human translation. Other applications include contemporaneous translation of text during live communication, in which signals can be first machine-translated, and then evaluated for a statistical assessment of confidence in translational accuracy, after which further data in the form of additional machine or human translation can be gathered.

Figure 1:
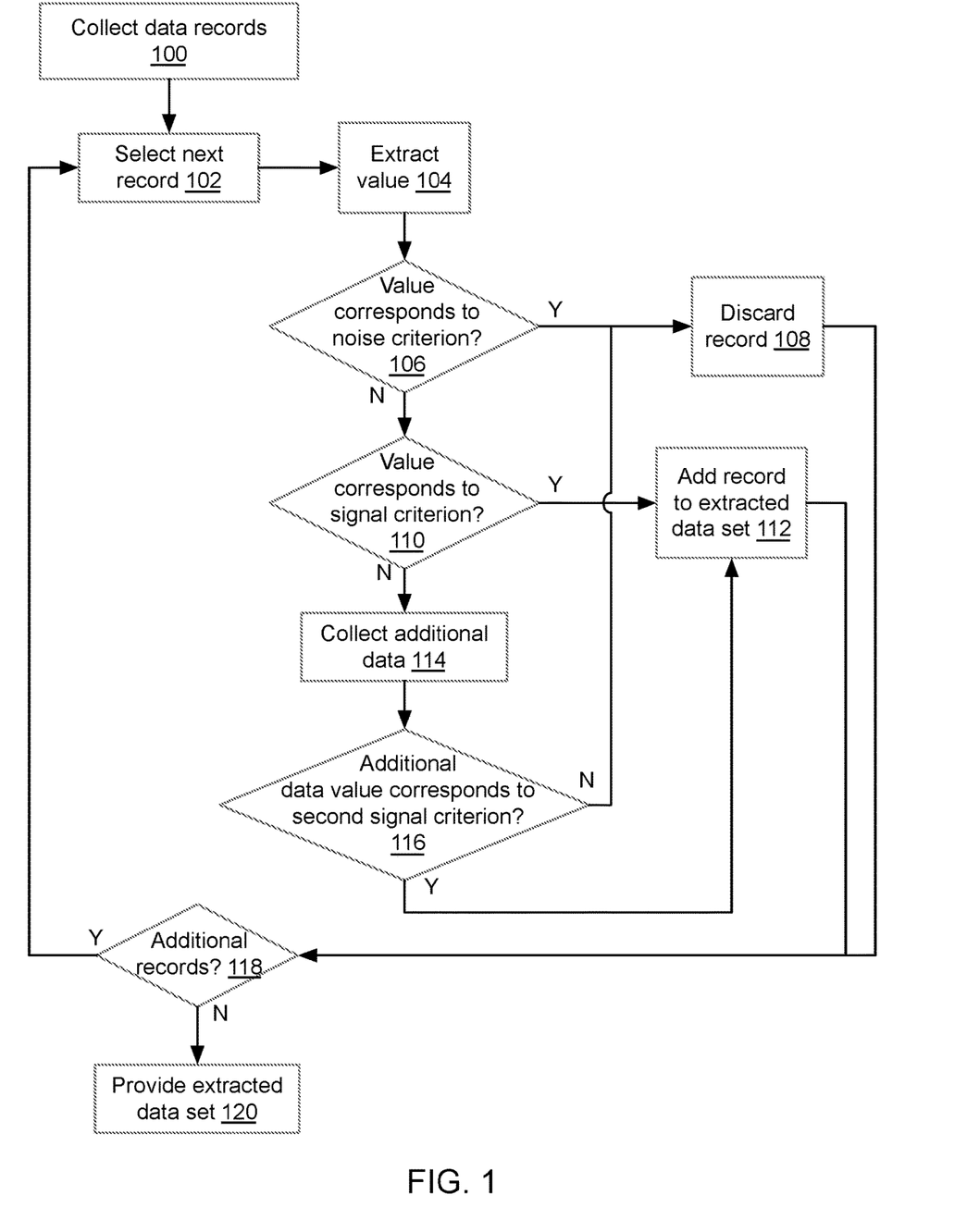
FIG. 1 is a flow chart of an implementation of a method for extraction of relevant signals from sparse data sets.

FIG. 1 is a flow chart of an implementation of a method for extraction of relevant signals from sparse data sets. At step 100, one or more data records from a first sparse data set may be collected. Each data record may comprise one or more identifiers, and one or more values. At step 102, a first record may be selected (e.g. in order, randomly, etc.), and at step 104, the associated one or more values extracted. At step 106, the system may determine whether the extracted values correspond to a predefined noise criterion. If so, then at step 108, the record may be discarded. If not, then at step 108, the system may determine whether the extracted values correspond to a predefined signal criterion. If so, then at step 112, the record may be added to an extracted data set of relevant data records.

However, as discussed above, in many instances, a value may not immediately be identifiable as corresponding to a noise criterion or signal criterion, particularly with signals in sparse data sets. Accordingly, in such instances, at step 114, additional data may be collected from at least one additional data set, which may or may not be a sparse data set. The additional data may be associated with the first data record, the identifier of the first data record, and/or the values of the first data record. The additional data may comprise at least a second value. The second value may be compared to a second predefined signal criterion at step 116. If the second value does not correspond to the second predefined signal criterion, then the data record may be discarded at step 108; otherwise, the record may be added to the relevant data set at step 112. Steps 102-118 may be repeated iteratively for each additional data record in the first sparse data set. Upon completion, at step 120, the extracted data set of relevant data records may be provided.

Having discussed the specifics of embodiments of the systems and methods of extraction of signals from sparse data sets, it may be helpful to discuss the computing environments in which such embodiments may be deployed.

Figure 2:
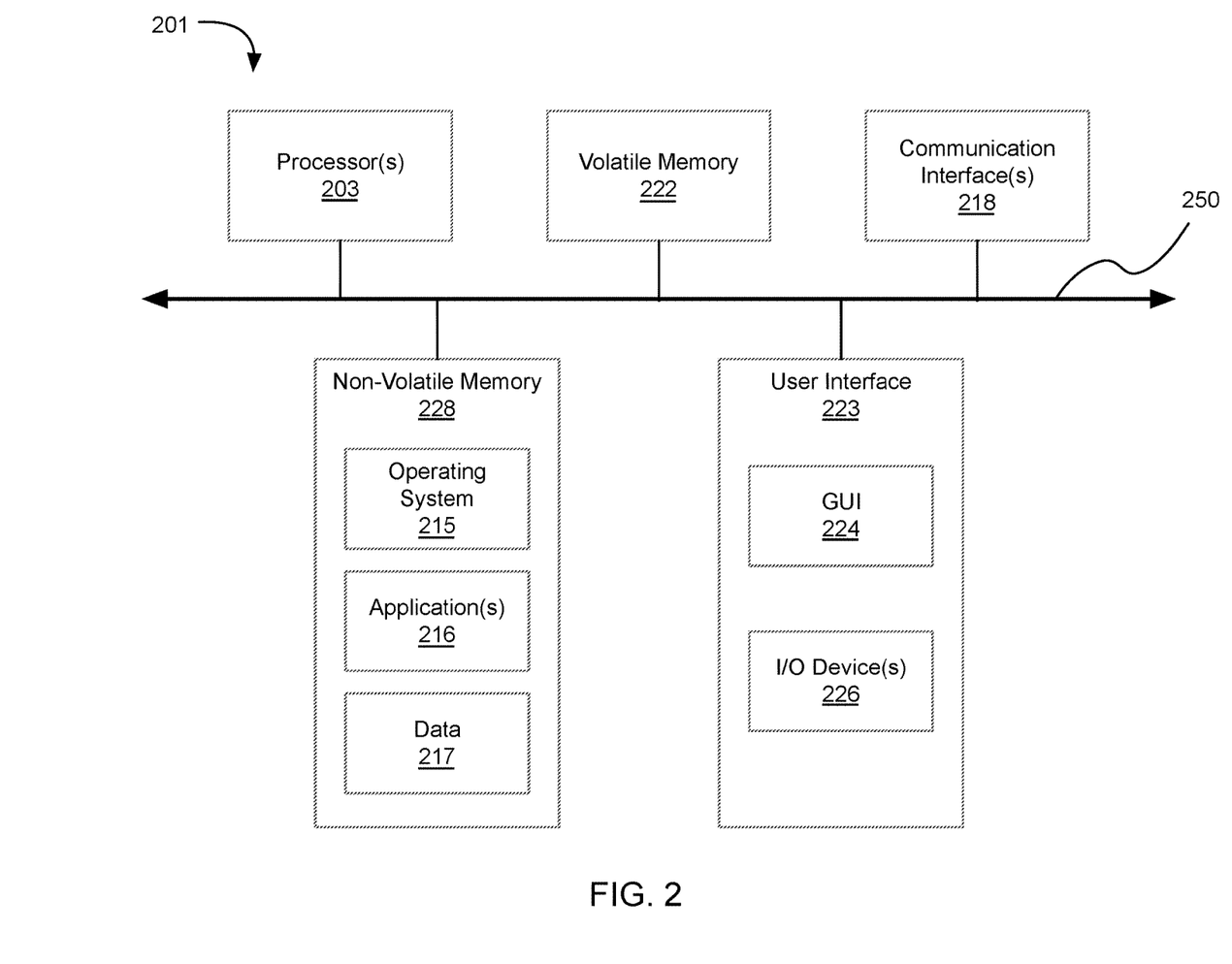
FIG. 2 is a block diagram illustrating an implementation of a computing environment for use with the systems and methods discussed herein.

As shown in FIG. 2, computer 201 may include one or more processors 203, volatile memory 222 (e.g., random access memory (RAM)), non-volatile memory 228 (e.g., one or more hard disk drives (HDDs) or other magnetic or optical storage media, one or more solid state drives (SSDs) such as a flash drive or other solid state storage media, one or more hybrid magnetic and solid state drives, and/or one or more virtual storage volumes, such as a cloud storage, or a combination of such physical storage volumes and virtual storage volumes or arrays thereof), user interface (UI) 223, one or more communications interfaces 218, and communication bus 250. User interface 223 may include graphical user interface (GUI) 224 (e.g., a touchscreen, a display, etc.) and one or more input/output (I/O) devices 226 (e.g., a mouse, a keyboard, a microphone, one or more speakers, one or more cameras, one or more biometric scanners, one or more environmental sensors, one or more accelerometers, etc.). Non-volatile memory 228 stores operating system 215, one or more applications 216, and data 217 such that, for example, computer instructions of operating system 215 and/or applications 216 are executed by processor(s) 203 out of volatile memory 222. In some embodiments, volatile memory 222 may include one or more types of RAM and/or a cache memory that may offer a faster response time than a main memory. Data may be entered using an input device of GUI 224 or received from I/O device(s) 226. Various elements of computer 201 may communicate via one or more communication buses, shown as communication bus 250.

Computer 201 as shown in FIG. 2 is shown merely as an example, as clients, servers, intermediary and other networking devices and may be implemented by any computing or processing environment and with any type of machine or set of machines that may have suitable hardware and/or software capable of operating as described herein. Processor (s) 203 may be implemented by one or more programmable processors to execute one or more executable instructions, such as a computer program, to perform the functions of the system. As used herein, the term "processor" describes circuitry that performs a function, an operation, or a sequence of operations. The function, operation, or sequence of operations may be hard coded into the circuitry or soft coded by way of instructions held in a memory device and executed by the circuitry. A "processor" may perform the function, operation, or sequence of operations using digital values and/or using analog signals. In some embodiments, the "processor" can be embodied in one or more application specific integrated circuits (ASICs), microprocessors, digital signal processors (DSPs), graphics processing units (GPUs), microcontrollers, field programmable gate arrays (FPGAs), programmable logic arrays (PLAs), multi-core processors, or general-purpose computers with associated memory. The "processor" may be analog, digital or mixed-signal. In some embodiments, the "processor" may be one or more physical processors or one or more "virtual" (e.g., remotely located or "cloud") processors. A processor including multiple processor cores and/or multiple processors multiple processors may provide functionality for parallel, simultaneous execution of instructions or for parallel, simultaneous execution of one instruction on more than one piece of data.

Communications interfaces 218 may include one or more interfaces to enable computer 201 to access a computer network such as a Local Area Network (LAN), a Wide Area Network (WAN), a Personal Area Network (PAN), or the Internet through a variety of wired and/or wireless or cellular connections.

In described embodiments, the computing device 201 may execute an application on behalf of a user of a client computing device. For example, the computing device 201 may execute a virtual machine, which provides an execution session within which applications execute on behalf of a user or a client computing device, such as a hosted desktop session. The computing device 201 may also execute a terminal services session to provide a hosted desktop environment. The computing device 201 may provide access to a computing environment including one or more of: one or more applications, one or more desktop applications, and one or more desktop sessions in which one or more applications may execute.

It should be noted that certain passages of this disclosure may reference terms such as "first" and "second" in connection with devices, mode of operation, transmit chains, antennas, etc., for purposes of identifying or differentiating one from another or from others. These terms are not intended to merely relate entities (e.g., a first device and a second device) temporally or according to a sequence, although in some cases, these entities may include such a relationship. Nor do these terms limit the number of possible entities (e.g., devices) that may operate within a system or environment.

It should be understood that the systems described above may provide multiple ones of any or each of those components and these components may be provided on either a standalone machine or, in some embodiments, on multiple machines in a distributed system. In addition, the systems and methods described above may be provided as one or more computer-readable programs or executable instructions embodied on or in one or more articles of manufacture. The article of manufacture may be a hard disk, a CD-ROM, a flash memory card, a PROM, a RAM, a ROM, or a magnetic tape. In general, the computer-readable programs may be implemented in any programming language, such as LISP, PERL, C, C++, C#, PROLOG, or in any byte code language such as JAVA. The software programs or executable instructions may be stored on or in one or more articles of manufacture as object code.

While the foregoing written description of the methods and systems enables one of ordinary skill to make and use what is considered presently to be the best mode thereof, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

While various embodiments of the methods and systems have been described, these embodiments are illustrative and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the illustrative embodiments and should be defined in accordance with the accompanying claims and their equivalents.

What is claimed is:

1. A method, comprising:
 collecting, by one or more processors, first data from a first sparse data set on a first genetic variant database corresponding to one or more populations of subjects, at least one item in the first data in the first sparse data set comprising a first identifier corresponding to a genetic variant associated with a disease of interest for screening;
 determining, by the one or more processors, a first number of items in the first data in the first sparse data set having the first identifier, wherein the first number of items in the first data of the first sparse data set is at least two orders of magnitude less than a second number of items in the first data of the first sparse data set having null values; and
 collecting, by the one or more processors, second data from at least one second sparse data set on a second genetic variant database, responsive to the first number of items of data being below a predefined threshold, the at least one second sparse data set comprising data corresponding to at least one item of data in the first sparse data set, wherein each item of data in the at least one second sparse data set lacks the first identifier, wherein a third number of items in the second data of the at least one second sparse data set is at least two orders of magnitude less than a fourth number of items in the second data of the at least one second sparse data set having null values;
 generating, by the one or more processors, for storage on a storage unit, an extracted data set including the first data of the first sparse data set and the second data from the at least one second sparse data set; and
 identifying, by the one or more processors using the extracted data set, from the one or more populations of subjects, a subject as a potential carrier of the disease of interest associated with the genetic variant for the screening.

2. The method of claim 1, wherein the first genetic variant database or the second genetic variant database comprises human genetic variant data.

3. The method of claim 2, wherein each item of data comprises information identifying the genetic variant, wherein the first identifier comprises an indication of loss-of-function status corresponding to the genetic variant identified in the item of data.

4. A method for extracting relevant signals from sparse data sets, comprising performing the method of claim 1 with a first set of parameters to generate a first set of relevant signals; and performing the method of claim 1 at least one second time with at least one second set of parameters to generate at least one second set of relevant signals.

5. A method, comprising:
 collecting, by one or more processors, a plurality of data records from a first sparse data set on a first genetic variant database corresponding to one or more populations of subjects, each data record of the plurality of records comprising a first identifier and at least one first value, wherein a first number of records of the first sparse data set is at least two orders of magnitude less than a second number of records in the first sparse data set having null values; and
 for each data record:
  comparing, by the one or more processors, the at least one first value with (i) a first predefined signal criterion defining a genetic variant and (ii) a first predefined noise criterion defining a frequency range for the genetic variant; and
  when the at least one first value corresponds to the first predefined noise criterion, discarding the data record; and
  when the at least one first value does not correspond to either the first predefined signal criterion or the first predefined noise criterion:
   collecting, by the one or more processors, second data from at least one second sparse data set on one or more second genetic variant databases, the at second data comprising a second identifier corresponding to the first identifier of the data record and at least one second value identifying a count of data containing the genetic variant, wherein a third number of items in the second data of the at least one second sparse data set is at least two orders of magnitude less than a fourth number of items in the second data of the at least one second sparse data set having null values;
   comparing, by the one or more processors, the at least one second value with a second predefined signal criterion defining a threshold for the count of data; and
   adding, by the one or more processors, to an extracted data set, the second data record responsive to the at least one second value corresponding to the second predefined signal criterion; and
  providing, by the one or more processors, for storage on a storage unit, the extracted data set;
  identifying, by the one or more processors using the extracted data set, from the one or more populations of subjects, a subject as a potential carrier of a disease of interest associated with the genetic variant for screening.

6. The method of claim 5, wherein the first genetic variant database or the second genetic variant database comprises human genetic variant data.

7. The method of claim 6, wherein the at least one first value corresponds to an indication of a phenotype of the genetic variant.

8. The method of claim 5, wherein the first predefined signal criterion comprises an indication of a loss-of-function phenotype corresponding to the genetic variant; or wherein the first predefined signal criterion comprises an indication of a pathogenic phenotype corresponding to the genetic variant.

9. A method for extracting relevant signals from sparse data sets, comprising performing the method of claim 5 with a first set of parameters to generate a first set of relevant signals; and performing the method of claim 5 at least one second time with at least one second set of parameters to generate at least one second set of relevant signals.

10. A system, comprising:
one or more processors coupled with memory, configured to:
collect a plurality of data records from a first sparse data set comprising a plurality of data records on a first genetic variant database corresponding to one or more populations of subjects, each data record of the plurality of records comprising a first identifier and at least one first value, wherein a first number of records of the first sparse data set is at least two orders of magnitude less than a second number of records in the first sparse data set having null values;
for each data record:
compare the at least one value with (ii) a first predefined signal criterion defining a genetic variant and (ii) a first predefined noise criterion defining a frequency range for the genetic variant; and
when the at least one first value corresponds to the first predefined noise criterion, discard the data record; and
when the at least one first value does not correspond to either the first predefined signal criterion or the first predefined noise criterion:
collect second data from at least one second sparse data set on one or more second genetic variant databases, the second data comprising a second identifier corresponding to the first identifier of the data record and a second value, the second value identifying a count of data containing the genetic variant, wherein a third number of items in the second data of the at least one second sparse data set is at least two orders of magnitude less than a fourth number of items in the second data of the at least one second sparse data set having null values;
compare the at least one second value with a second predefined signal criterion defining a threshold for the count of data; and
add, to an extracted data set, the data record responsive to the at least one second value corresponding to the second predefined signal criterion; and
provide, for storage on a storage unit, the extracted data set;
identify, using the extracted data set, from the one or more populations of subjects, a subject as a potential carrier of a disease of interest associated with the genetic variant for screening.

11. The system of claim 10, wherein the genetic variant database comprises human genetic variant data;
wherein the at least one second genetic variant database comprises human genetic variant data;
or
wherein the at least one first value corresponds to an indication of a phenotype of the genetic variant.

12. The system of claim 11, wherein the first predefined signal criterion comprises an indication of a loss-of-function phenotype corresponding to the genetic variant; or
wherein the first predefined signal criterion comprises an indication of a pathogenic phenotype corresponding to the genetic variant.

13. A system, comprising:
one or more processors coupled with memory, configured to:
collect first data from a first sparse data set on a first genetic variant database corresponding to one or more populations of subjects, at least one item in the first data in the first sparse data set comprising a first identifier corresponding to a genetic variant associated with a disease of interest for a screening;
determine a first number of items in the first data in the first sparse data set having the first identifier, wherein the first number of items in the first data of the first sparse data set is at least two orders of magnitude less than a second number of items in the first data of the first sparse data set having null values;
collect second data from at least one second sparse data set on a second genetic variant database, responsive to the first number of items of data being below a predefined threshold, the at least one second sparse data set comprising second data corresponding to at least one item of data in the first sparse data set, wherein each item of data in the at least one second sparse data set lacks the first identifier, wherein a third number of items in the second data of the at least one second sparse data set is at least two orders of magnitude less than a fourth number of items in the second data of the at least one second sparse data set having null values; and
generate, for storage on a storage unit, an extracted data set including the first data of the first sparse data set and the second data from the at least one second sparse data set; and
identify, from the one or more populations of subjects, a subject as a potential carrier of the disease of interest associated with the genetic variant for the screening, using the extracted data set.

14. The system of claim 13, wherein the first genetic variant database comprises human genetic variant data, or wherein the second genetic variant database comprises human genetic variant data.

15. The system of claim 14, wherein the first identifier comprises an indication of loss-of-function status corresponding to the genetic variant identified in the item of data.

* * * * *